United States Patent
Watson

(10) Patent No.: US 8,376,980 B2
(45) Date of Patent: Feb. 19, 2013

(54) INGROWTH PREVENTING INDWELLING CATHETER ASSEMBLY

(76) Inventor: David A. Watson, San Jose, CA (US)

(*) Notice: Subject to any disclaimer, the term of this patent is extended or adjusted under 35 U.S.C. 154(b) by 67 days.

(21) Appl. No.: 12/730,434

(22) Filed: Mar. 24, 2010

(65) Prior Publication Data

US 2010/0179471 A1    Jul. 15, 2010

Related U.S. Application Data

(62) Division of application No. 11/013,984, filed on Dec. 15, 2004, now Pat. No. 7,763,142, which is a division of application No. 10/087,578, filed on Feb. 28, 2002, now abandoned.

(60) Provisional application No. 60/272,722, filed on Mar. 1, 2001.

(51) Int. Cl.
*A61M 5/00* (2006.01)
*A61M 25/00* (2006.01)

(52) U.S. Cl. ............ 604/8; 604/9; 604/524; 604/526

(58) Field of Classification Search ........... 604/6.16, 604/8, 9, 507, 523, 524, 526, 527
See application file for complete search history.

(56) References Cited

U.S. PATENT DOCUMENTS

| | | | |
|---|---|---|---|
| 3,020,913 A | | 2/1962 | Heyer |
| 3,690,323 A | | 9/1972 | Wortman et al. |
| 3,710,781 A | | 1/1973 | Huthcins, IV et al. |
| 4,445,891 A | | 5/1984 | Patel |
| 4,601,724 A | * | 7/1986 | Hooven et al. ............ 604/264 |
| 4,737,153 A | * | 4/1988 | Shimamura et al. ....... 604/526 |
| 4,767,400 A | | 8/1988 | Miller et al. |
| 4,950,224 A | | 8/1990 | Gorsuch et al. |
| 4,950,232 A | | 8/1990 | Ruzicka et al. |
| 4,985,022 A | | 1/1991 | Fearnot et al. |
| 5,069,674 A | * | 12/1991 | Fearnot et al. ............ 604/524 |
| 5,074,849 A | | 12/1991 | Sachse |
| 5,152,743 A | | 10/1992 | Gorsuch et al. |
| 5,152,753 A | | 10/1992 | Laguette et al. |
| 5,154,693 A | | 10/1992 | East et al. |
| 5,178,158 A | | 1/1993 | de Toledo |
| 5,201,754 A | | 4/1993 | Crittenden et al. |
| 5,284,761 A | | 2/1994 | Aebischer et al. |
| 5,334,169 A | | 8/1994 | Brown et al. |
| 5,372,587 A | | 12/1994 | Hammerslag et al. |
| 5,405,316 A | * | 4/1995 | Magram ...................... 604/8 |
| 5,431,817 A | | 7/1995 | Braatz et al. |
| 5,462,523 A | | 10/1995 | Samson et al. |
| 5,547,472 A | | 8/1996 | Onishi et al. |
| 5,569,198 A | | 10/1996 | Racchini |
| 5,662,622 A | | 9/1997 | Gore et al. |
| 5,846,220 A | | 12/1998 | Elsberry |
| 5,980,480 A | | 11/1999 | Rubenstein et al. |
| 6,056,725 A | | 5/2000 | Elsberry |

(Continued)

FOREIGN PATENT DOCUMENTS

EP    0823262 A2 * 11/1998

OTHER PUBLICATIONS

David J. Gower, M.D., David Watson, Derek Harper, e-PTFE Ventricular Shunt Catheters, Neurosurgery, Dec. 1992, pp. 1132-1135, vol. 31, No. 6, University of Oklahoma Health Sciences Center, Oklahoma City, OK.

*Primary Examiner* — Leslie Deak
(74) *Attorney, Agent, or Firm* — Fulwider Patton LLP

(57) ABSTRACT

A surgically implantable delivery or drainage catheter assembly includes a porous fiber membrane that is permeable to the intended drainage or delivery fluid, yet has an outer surface morphology and porosity that prevents the ingrowth of tissue. The porous fiber membrane is created using a phase-inversion process which is controlled to select a desired porosity. A reinforcement member is also disposed within the porous fiber membrane.

18 Claims, 2 Drawing Sheets

U.S. PATENT DOCUMENTS

| | | |
|---|---|---|
| 6,074,374 A | 6/2000 | Fulton |
| 6,093,180 A | 7/2000 | Elsberry |
| 6,096,070 A * | 8/2000 | Ragheb et al. ............... 623/1.39 |
| 6,126,628 A | 10/2000 | Nissels |
| 6,152,912 A | 11/2000 | Jansen et al. |
| 6,206,824 B1 | 3/2001 | Ohara et al. |
| 6,315,757 B1 | 11/2001 | Chee et al. |
| 6,319,244 B2 | 11/2001 | Suresh et al. |
| 6,325,790 B1 | 12/2001 | Trotta |
| 6,336,924 B1 | 1/2002 | Lecuyer et al. |

\* cited by examiner

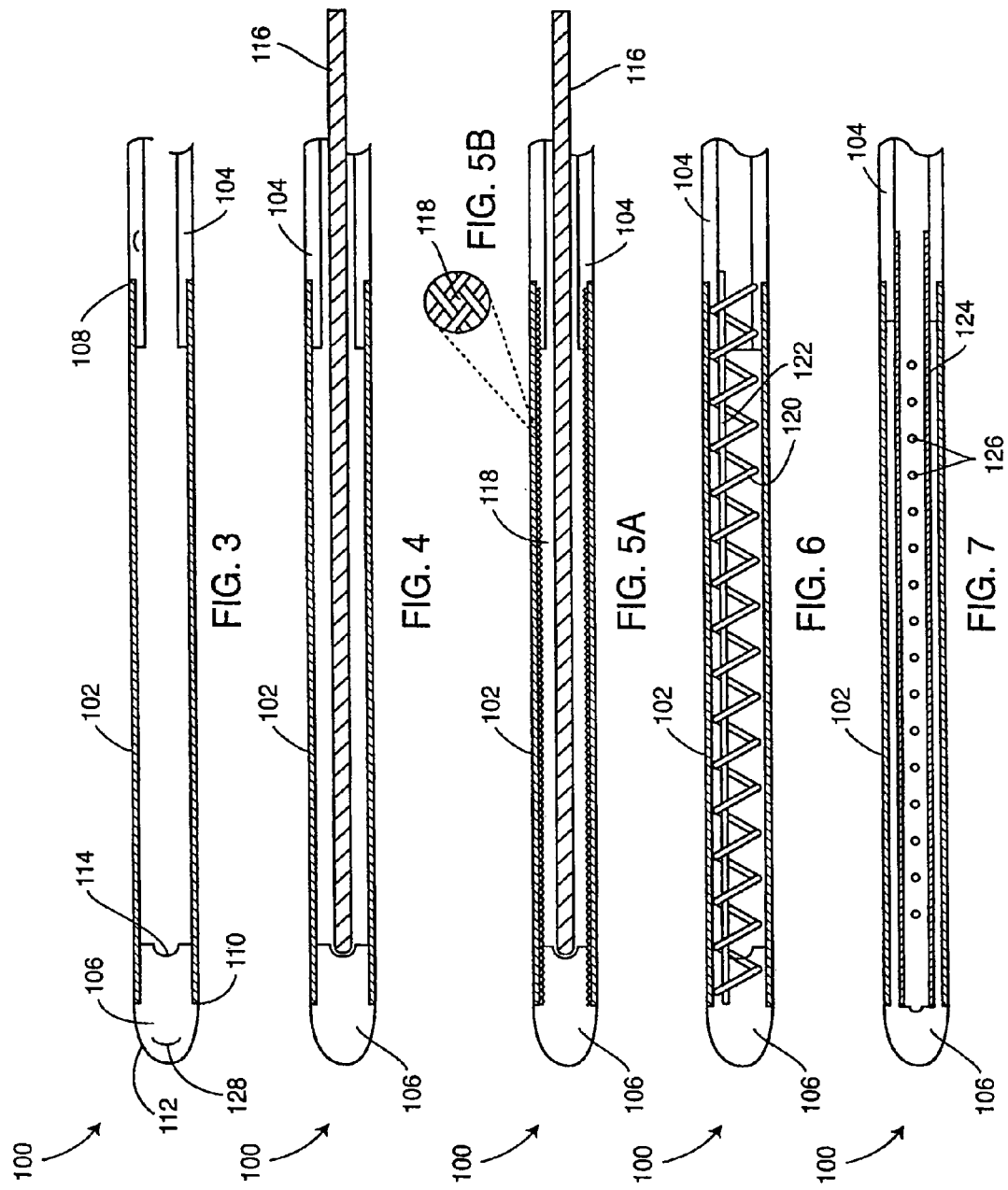

INGROWTH PREVENTING INDWELLING CATHETER ASSEMBLY

RELATED APPLICATIONS

This application is a divisional of co-pending application Ser. No. 11/013,984, filed on Dec. 15, 2004, which is a divisional application Ser. No. 10/087,578, filed on Feb. 28, 2002, which is based upon and claims priority from Provisional Application Ser. No. 60/272,722 filed Mar. 1, 2001, the entire contents of which are incorporated herein by reference.

BACKGROUND OF THE INVENTION

This invention relates generally to surgically implanted delivery and drainage catheters, such as in shunt systems that drain cerebrospinal fluid from the brain ventricles and drug delivery catheters implanted in fluid filled spaces or within the parenchyma of tissues. More particularly, this invention is an improved catheter that prevents the ingrowth of tissue and subsequent blockage of such catheter.

As is well known in the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in whom fluids which ought to drain away instead accumulate within the brain and thereby exert extreme pressure and skull deforming forces.

In treating hydrocephalus, cerebrospinal fluid accumulated in the brain ventricles is drained away by a catheter inserted into a ventricle through the skull, and the catheter is connected to a tube which conducts the fluid away from the brain to be reintroduced into the vascular system, as by extending through the patient's jugular vein to the atrium portion of the heart or to the peritoneul cavity of the abdomen. To control the flow of cerebrospinal fluid and maintain the proper pressure in the brain ventricle, a valve is generally placed in the conduit between the brain and the heart. The brain ventricles are normally large enough to easily accommodate an end of a catheter several millimeters in diameter. Such ventricular catheters are commonly provided with numerous small holes approximately 0.25-0.50 millimeters (250-500 micrometers) in diameter through their walls for receiving cerebrospinal fluid from the ventricle. To insert the ventricular catheter, a hole is bored through the skull and a solid stylet (such as that shown in U.S. Pat. No. 5,098,411) is utilized as an introducer to properly position the flexible catheter within the brain ventricle. Since the openings in the wall of the catheter are of substantial size, tissue can easily infiltrate them over time. Operative revisions to replace occluded ventricular catheters are quite common and are the leading cause of hydrocephalus shunt revisions.

Additionally, catheters are often placed within the ventricles of the brain, other fluid filled body cavities and/or directly within the tissues of the target organ for the purpose of targeted delivery of therapeutic substances. These catheters can also be infiltrated with tissue that compromises the flow of the drug being delivered.

In 1992, the inventor co-authored a paper (Neurosurgery, Vol. 31, No. 6, December 1992) on an attempted application of expanded polytetrafluoroethylene (e-PTFE) for the purposes of producing a catheter for use in hydrocephalus drainage that would be more resistive to bacterial colonization than the conventional silicone catheter. This paper described the failure of experimentation with a micro-porous e-PTFE catheter. E-PTFE was selected as a candidate material not for its porosity, but for its surface chemistry. E-PTFE was known to inhibit bacteria colonization, but was too stiff for a catheter material. For those prototype catheters, the e-PTFE was expanded to the minimum porosity that was technologically possible at the time, approximately 5 micrometers. Expanding the material retained its surface chemistry but greatly improved its flexibility. The expansion process of the e-PTFE yields a supple material like silicone whereas the unexpanded PTFE is too generally stiff for long-term implantation. As demonstrated in the paper, the catheter segments that were implanted with e-PTFE of 5 and 30 micrometers internodal distances occluded rapidly with tissue ingrowth.

Thus, catheters having a porosity of 5 micrometers or greater are unsuitable for indwelling catheters as they become occluded due to tissue ingrowth. It is important to emphasize that this paper was studying material properties that resisted bacterial colonization and the adverse reaction of tissue infiltration directly into the structure of the polymer was a finding that excluded porous materials for further consideration for that application. Because of this clinical failure, this paper taught away from the use of porous materials for hydrocephalus drainage applications.

Micro-porous membranes are commonly utilized in the field of cell encapsulation. In this application, the membrane is used to provide a means of isolating living cells within a closed capsule from the host immune system. The membrane in this application is permeable to body fluids, proteins, glucose, and the by-products of the encapsulated cells, yet impermeable to the host cells and large immune system molecules. Similar membranes are extensively used in the field of dialysis. In this application, a patient's blood is passed through the inner lumen of the membrane and only the cells or molecules of selected sizes are allowed to pass though the membrane and out of the patient's blood. The manufacture and control of the porosity of micro-porous hollow fiber membranes for use in such applications are suitably defined in the prior art, such as U.S. Pat. No. 5,284,761, which is incorporated by reference herein. In these applications, the porosity of the membrane is extremely small, yielding membranes unsuitable for the mass flow of fluids necessary to provide adequate drainage for hydrocephalus applications, wound drainage or drug delivery. Additionally, these membranes are extremely fragile with break forces generally less than 0.5 Newton (50 grams) making them unsuitable for conventional introduction into the body, as with indwelling catheters.

Accordingly, there has been a continuing need for an improved indwelling catheter that can provide continuous flow of fluids without allowing tissue infiltration. Such a catheter should be capable of being introduced conventionally, and it should be of simplified construction utilizing materials which are easily sterilizable and compatible for biomedical usage. The present invention fulfills these needs and provides other related advantages.

SUMMARY OF THE INVENTION

The present invention resides in an improved means for facilitating fluid flow through a catheter without providing passages into which tissue can infiltrate. The catheter assembly of the present invention generally comprises a length of non-porous flexible tubing having a tubular segment comprised of a porous fiber membrane that is permeable to drainage or delivery fluid, and impermeable to tissue in-growth. As such membranes are quite fragile and prone to collapse, a reinforcement member is disposed within the tubular membrane segment.

The porous fiber membrane tubing is formed so as to have a porosity of less than 5 micrometers in order to be impermeable to tissue ingrowth, while having a drainage or delivery fluid flow rate suitable for the intended application, typically between 5 millimeters and 100 millimeters per hour for hydrocephalus applications. In a particularly preferred embodiment, the porous tubing is created using a phase-inversion process which comprises the steps of dissolving a polymer in a first solution, and passing the first solution containing the dissolved polymer through an aperture into a coagulation bath chamber filled with a second solution in which the polymer is non-soluble to create a hollow fiber membrane tube. Typically, the polymer comprises polyether sulfone. The concentration of the polymer in the first solution, the flow of the first solution into the chamber of the second solution, or the temperature, is controlled to create a hollow fiber membrane tube having a porosity of less than 5 micrometers, and preferably between 1 and 2 micrometers. Such porosity allows the porous membrane to be permeable to drainage or delivery fluid, typically at a rate of approximately 20 milliliters per hour, while being impermeable to tissue in-growth.

The porous fiber membrane tubing has a first end attached to an end of the non-porous, typically silicone, tubing, and a second end attached to a catheter insertion tip. The tip preferably includes a rounded exterior end, and an interior end configured to fit a catheter introducer to facilitate introduction of the catheter into a brain ventricle or other area of the body. The end of the non-porous tubing is of reduced cross-sectional diameter, as is an interior end of the tip, so that attachment of the porous membrane segment maintains a generally uniform catheter assembly outer diameter.

A slit valve may be formed in the non-porous flexible tubing, or insertion tip, to relieve excessive drainage pressure in the event internal catheter fluid pressure builds faster than outflow through the porous segment.

Reinforcement of the porous membrane segment can be done in a variety of ways. For example, internal reinforcement of the membrane can be performed by placing a rigid tube having apertures through a side wall thereof into the porous membrane. Alternatively, the reinforcement member comprises a woven polymer sleeve. In yet another embodiment, the reinforcement member comprises a spring that may be associated with a rigid wire to facilitate introduction of the catheter within the body.

Use of the porous fiber membrane in the catheter assembly of the present invention allows a desired permeability to drainage or delivery fluids, while being impermeable to tissue in-growth. Thus, the flow of the drug being delivered or fluid being drained is not compromised, reducing the need to operatively revise and replace the catheters.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a fragmented, partially sectional view of a catheter assembly having a segment of porous fiber membrane in accordance with the present invention;

FIG. 4 is a fragmented, partially sectional view taken generally along line 4-4 of FIG. 2, FIG. 5A is a fragmented, partially sectional view similar to FIG. 4, of an embodiment in which the hollow-fiber membrane is internally reinforced with a woven polymer sleeve;

FIG. 5B is an enlarged view of a portion of the woven polymer sleeve of FIG. 5A;

FIG. 6 is a fragmented partially sectional view similar to FIGS. 4 and 5A, of another embodiment in which the hollow-fiber membrane is internally reinforced with a coiled spring; and FIG. 7 is a fragmented, partially sectional view similar to FIGS. 4, 5A and 6, of yet another embodiment in which the hollow-fiber membrane is internally reinforced with a perforated rigid tube.

DETAILED DESCRIPTION OF THE PREFERRED EMBODIMENTS

Figure 1:
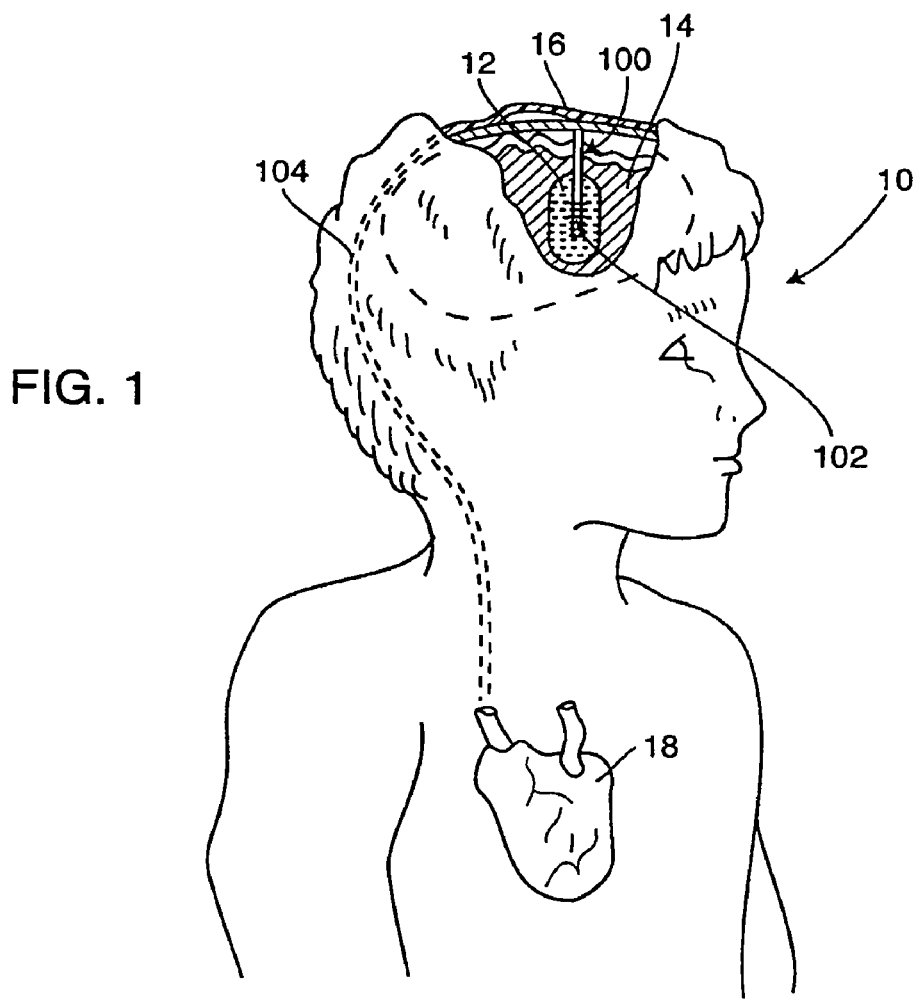
FIG. 1 is a perspective view, partially in section, of a patient having an implanted hydrocephalus system employing a catheter assembly embodying the present invention.

As shown in the drawings for purposes of illustration, the present invention is concerned with an improved catheter assembly, generally designated in the accompanying drawings by the reference number 100, that is capable of being implanted into a patient for purposes of draining or delivering fluids to or from a target area while resisting tissue in-growth.

With reference to FIG. 1, a patient 10 is illustrated having a catheter assembly 100 embodying the present invention implanted therein as a hydrocephalus system. As described above, and is well known in the prior art, cerebrospinal fluid 12 accumulates in brain ventricles 14 and must be drained away by a catheter 100 inserted into a ventricle 14 through the skull 16. In the present invention, a porous segment 102 of the catheter assembly 100 is placed within the ventricle 14 and which is permeable to the fluid 12. The porous segment 102 is connected to a non-porous, and typically silicone, tubing 104 which drains the fluid 12 from the ventricles 14 to a drainage location within the body, typically the atrium portion of the heart 18, or peritoneal cavity of the abdomen. The non-porous connective tubing 104 provides a fluid conduit to any number of other components, such as but not limited to, control valves for hydrocephalus or medication delivery pumps (not shown).

Figure 2:
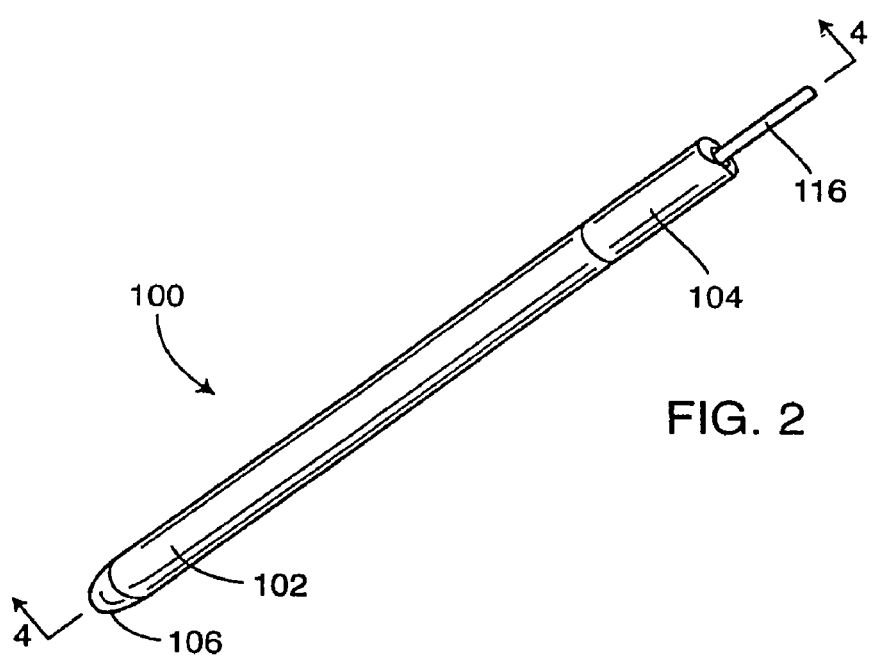
FIG. 2 is a fragmented perspective view of a catheter assembly embodying the present invention, and having an introducer inserted therein.

With reference to FIGS. 2 and 3, the catheter assembly 100 is generally constructed of non-porous connective tubing 104, and a non-porous distal tip 106 which are integrally attached to opposite ends of a segment of hollow fiber membrane 102 having a selected porosity. The hollow fiber membrane tubing segment 102 is comprised of a porous material that is permeable to the intended drainage or delivery fluid, yet has an outer surface morphology that prevents the in-growth of host tissue. The manufacture of catheter assemblies 100 from such membrane 102 to prevent tissue ingrowth while allowing suitable fluid flow therethrough is of particular importance to the invention.

Although the porous segment 102 may be produced using a variety of processes, in a particularly preferred embodiment, the porous segment 102 is produced using a polymer phase-inversion process. In such process, a polymer (such as Polyether Sulfone (PES)) is fully dissolved in a fluid in which the polymer is soluble (such as DMSO). This solution is passed through an aperture and forced to flow into a second fluid filled chamber (coagulation bath). The coagulation bath contains a fluid in which the polymer solvent is miscible yet is not also a solvent for the polymer (such as water). When the polymer dispersion flows into the coagulation bath, the solvent spontaneously flows out of the polymer and the polymer solidifies in the shape of the aperture. For hollow-fiber applications, the aperture is an annular space between two concentric tubes. A second inter-lumenal fluid (generally that within the coagulation bath) is also provided within the inner concentric tube such that the polymer solvent can dissipate centrally as well as externally. The result of the process is a hollow fiber membrane tube of a selected length.

In hydrocephalus applications, the porous hollow fiber membrane tube 102 must be able to provide for a certain range of cerebrospinal fluid flow per hour. Such cerebrospinal fluid flow varies depending upon conditions, such as REM sleep, sudden movement, etc. Although the catheter assembly 100 must be able to provide for an average of 20 milliliters of cerebrospinal fluid flow per hour with a head pressure of only 5 to 10 centimeters of water pressure, the fluid flow rate can vary from 5 milliliters to 100 milliliters per hour. The porous hollow fiber membrane section 102 must also be impermeable to tissue in-growth. As such, the porous segment 102 must have a porosity of less than 5 micrometers, and preferably 1 to 2 micrometers. The surface structure and porosity of hollow-fiber membranes can be adjusted by changing the processing parameters (such as solvents used, coagulation bath and inter-lumenal fluids used, temperature, pressure and speed) of the process.

Thus, it will readily apparent to one skilled in the art that the present invention resides in the selection and manufacture of appropriate membrane properties and the application and construction of these membranes into suitable catheters for the purpose of providing fluid flow to or from a body site without allowing tissue infiltration. Based on findings in the field of cell encapsulation, it has been determined that membranes with less than 5 micrometer pore structure do not encourage brain tissue ingrowth. Furthermore, these materials can be engineered (as described above) to provide adequate flow of saline-like body fluids to be efficacious for drainage (or for drug delivery applications) without the need for the large perforations that tissue can infiltrate.

With reference to FIGS. 2-4, once the selected length of porous hollow fiber membrane 102 is created, it is attached at one end thereof to the non-porous connective tubing 104. The connective tubing 104 may be comprised of any of a number of medical grade catheter material, such as polyurethane or silicone. Preferably, the point of attachment of the nonporous connective tubing 104 is of reduced cross-sectional diameter to form a shoulder 108 which fits within the inner diameter of the porous tubular segment 102 and creates a generally uniform outer diameter.

The opposite end of the porous segment 102 is connected to the tip 106. The tip 106 may be constructed entirely of the adhesive that is used to bond the porous segment 102 to the connective non-porous tubing 104, or alternatively be formed of a polymer component that is bonded to the porous fiber membrane 102 using adhesive. Preferably, the tip 106 also includes an area of reduced cross-sectional diameter to form a shoulder 110 acting as an attachment point for the hollow fiber membrane 102, and maintaining the generally uniform cross-sectional diameter and outer surface area to facilitate the introduction of the catheter 100 into the selected site within the patient 10. Also, the tip 106 preferably includes a rounded exterior end 112 to facilitate introduction of the catheter 100 to the selected site without damaging organs or tissue. In a particularly preferred embodiment, an interior end 114 of the tip 106 is formed to fit or receive an introducer 116, such as that illustrated in FIG. 4, which is used to insert the catheter 100 into the desired position within the patient for fluid drainage or drug delivery.

As is well known in the art, such introducers 116 are inserted into the catheter assembly and deformed according to the path to be taken by the catheter and subsequently removed once the catheter is implanted. Thus, the introducer 116, when used to place the catheter assembly 100, is placed in the inter-lumen of the catheter until it abuts the inside of the distal tip 106 at point 114 which is formed to receive the end of the introducer 116. The introducer 116 is then used to advance the catheter 100 into position and removed after proper placement.

As previously noted, phase-inversion produced membranes are generally quite fragile and cannot withstand the tensile forces of conventional introduction, such as the illustrated introducer 116. The invention rectifies this problem by providing an inner support for the porous membrane 102.

With reference now to FIGS. 5A and 5B, in a first preferred embodiment, reinforcement of the porous hollow fiber membrane tubular segment 102 is provided by means of a woven polymer sleeve 118. The internal sleeve 118 is secured to the tip 106 and connective non-porous tubing 104 such that it provides tensile strength to the porous segment 102 when the stylet 116 is introduced into the inter-lumen of the catheter 100. Such sleeves can be comprised of polymer strands (such as polyester) and can be woven into a tubular sleeve smaller in diameter than the internal diameter of the porous membrane 102. Such sleeves are easily constructed by those skilled in the art and are extremely strong in tensile strength.

With reference to FIG. 6, alternatively, a coiled spring 120 can be placed within the porous hollow fiber membrane 102 to provide the necessary reinforcement. A tensile wire 122 is preferably associated with the spring 120 and they are integrally attached to the tip 106 and connective tubing 104 with adhesive. The spring 120 prevents the hollow fiber membrane 102 from collapsing, and the tensile wire 122 provides the necessary tensile strength for placement.

With reference now to FIG. 7, in yet another embodiment, the central reinforcing element is a rigid tubing integrally attached at the tip 106 and connective tubing 104 and placed within the porous fiber membrane segment 102. The rigid tubing 124 includes a plurality of apertures 126 which allows the fluid to flow into or out of the porous membrane segment 102. These apertures 126 can be relatively large as the tube 124 is placed within the porous fiber membrane segment 102 and will not come into contact with surrounding tissue.

With reference again to FIG. 3, there may be certain instances where the rate of fluid to be delivered or the amount of fluid to be drained exceeds the capability of the hollow fiber membrane segment 102. For example, in hydrocephalus applications, during REM sleep it is well known that the amount of cerebrospinal fluid rises dramatically. The porosity of the hollow fiber membrane 102 may be insufficient to adequately drain the cerebrospinal fluid produced during these peak times. Thus, a relief valve 128 may be formed in either the tip 106 or the non-porous connective tubing 104 in the form of a slit valve which opens above a predetermined pressure to allow the entry or exit of fluids into or without the catheter assembly 100. Such slit valves 128 are similar to a one-way-valve and can be formed so as to normally be closed unless a predefined pressure differential is exceeded, at which point the slit valve 128 either opens inwardly or outwardly to facilitate the fluid flow.

It will be readily apparent to one skilled in the art that the catheter assembly 100 of the present invention provides many benefits to implanted catheter assemblies. The porous segment 102 is impermeable to tissue growth, yet is permeable to fluid drainage or fluid delivery at a range of fluid flow rates which can be altered during the formation of the hollow fiber membrane segment 102, as described above. Reinforcement of the hollow fiber membrane segment 102 allows the catheter assembly 100 to be placed in the target site using conventional means, such as the illustrated stylet 116. It is anticipated that the need for operative revisions and replacement of occluded ventricular catheters, and other implanted catheters, will be significantly reduced by the incorporation of the catheter assembly 100 of the present invention.

Although several embodiments of the invention have been described in detail for the purposes of illustration, various modifications may be made without departing from the spirit and scope of the invention. Accordingly, the invention is not to be limited, except as by the appended claims.

What is claimed is:

1. A segmented ingrowth preventing indwelling catheter assembly, the ingrowth preventing indwelling catheter assembly having a distal end configured to be placed within a brain ventricle for drainage of cerebrospinal fluid, the ingrowth preventing indwelling catheter assembly comprising:
   a first segment of porous fiber membrane tubing having a porosity of less than 5 micrometers so as to be impermeable to tissue ingrowth and having a drainage or delivery fluid-flow rate appropriate for an intended application;
   a second segment including a non-porous tip having a proximal end attached to a first end of the first segment of porous fiber membrane tubing to form the distal end of the ingrowth preventing indwelling catheter assembly, the proximal end of said second segment terminating at said first end of said first segment;
   a third segment of non-porous and flexible tubing having a distal end attached to a second end of the first segment of porous fiber membrane tubing, the distal end of said third segment terminating at said second end of said first segment, wherein said second segment is overlapping with said first segment at said first end of said first segment and said third segment is overlapping with said first segment at said second end of said first segment; and
   a rigid tubular reinforcement member having a plurality of apertures therethrough disposed within the first segment of porous fiber membrane tubing, said tubular reinforcement member being attached between said second segment including said non-porous tip and said third segment of non-porous and flexible tubing.

2. The assembly of claim 1, wherein an interior end of the non-porous tip is formed to fit a catheter introducer.

3. The assembly of claim 1, wherein said non-porous and flexible tubing includes a shoulder to maintain a generally uniform catheter assembly outer diameter.

4. The assembly of claim 1, wherein the porous fiber membrane tubing has a fluid-flow rate of up to 100 milliliters per hour.

5. The assembly of claim 1, wherein the porous fiber membrane tubing has a fluid flow rate of approximately 20 milliliters per hour.

6. The assembly of claim 1, wherein said porous fiber membrane tubing has a porosity of a porosity of between 1 and 2 micrometers.

7. The assembly of claim 1, wherein the porous fiber membrane tubing is formed of a polymer.

8. The assembly of claim 7, wherein the polymer comprises polyether sulfone.

9. A segmented ingrowth preventing indwelling catheter assembly, the ingrowth preventing indwelling catheter assembly having a distal end configured to be placed within a brain ventricle for drainage of cerebrospinal fluid, the ingrowth preventing indwelling catheter assembly comprising:
   a first segment of porous fiber membrane tubing having a porosity of less than 5 micrometers so as to be impermeable to tissue ingrowth and having a drainage or delivery fluid-flow rate appropriate for an intended application;
   a second segment including a non-porous tip having a proximal end attached to a first end of the first segment of porous fiber membrane tubing to form the distal end of the ingrowth preventing indwelling catheter assembly, the proximal end of said second segment terminating at said first end of said first segment;
   a third segment of non-porous and flexible tubing having a distal end attached to a second end of the first segment of porous fiber membrane tubing, the distal end of said third segment terminating at said second end of said first segment; and
   a woven polymer sleeve reinforcement member having a plurality of apertures therethrough disposed within the first segment of porous fiber membrane tubing, said woven polymer sleeve reinforcement member being attached between said second segment including said non-porous tip and said third segment of non-porous and flexible tubing, wherein the distal end of said woven polymer sleeve reinforcement member terminates within the proximal end of said second segment and the proximal end of said woven polymer sleeve reinforcement member terminates within the distal end of said third segment.

10. A segmented ingrowth preventing indwelling catheter assembly, the ingrowth preventing indwelling catheter assembly having a distal end configured to be placed within a brain ventricle for drainage of cerebrospinal fluid, the ingrowth preventing indwelling catheter assembly comprising:
   a first segment of porous fiber membrane tubing having a porosity of less than 5 micrometers so as to be impermeable to tissue ingrowth and having a drainage or delivery fluid-flow rate appropriate for an intended application;
   a second segment including a non-porous tip having a proximal end attached to a first end of the first segment of porous fiber membrane tubing to form the distal end of the ingrowth preventing indwelling catheter assembly, the proximal end of said second segment terminating at said first end of said first segment;
   a third segment of non-porous and flexible tubing having a distal end attached to a second end of the first segment of porous fiber membrane tubing, the distal end of said third segment terminating at said second end of said first segment; and
   a reinforcement member disposed within the first segment of porous fiber membrane tubing, said reinforcement member including a coiled spring and a tensile wire associated with the coiled spring, said coiled spring and tensile wire being attached between said second segment including said non-porous tip and said third segment of non-porous and flexible tubing, said coiled spring having a distal end and a proximal end and said tensile wire associated with the coiled spring having a distal end and a proximal end, wherein the distal end of said coiled spring and the distal end of said tensile wire reinforcement member terminate within the proximal end of said second segment and the proximal end of said coiled spring and the proximal end of said tensile wire reinforcement member terminate within the distal end of said third segment.

11. The assembly of claim 10, wherein an interior end of the non-porous tip is formed to fit a catheter introducer.

12. The assembly of claim 10, wherein said non-porous and flexible tubing includes a shoulder to maintain a generally uniform catheter assembly outer diameter.

13. The assembly of claim 10, wherein the porous fiber membrane tubing has a fluid-flow rate of up to 100 milliliters per hour.

14. The assembly of claim 10, wherein the porous fiber membrane tubing has a fluid flow rate of approximately 20 milliliters per hour.

15. The assembly of claim 10, wherein said porous fiber membrane tubing has a porosity of a porosity of between 1 and 2 micrometers.

16. The assembly of claim 10, wherein the porous fiber membrane tubing is formed of a polymer.

17. The assembly of claim 16, wherein the polymer comprises polyether sulfone.

18. A segmented ingrowth preventing indwelling catheter assembly, the ingrowth preventing indwelling catheter assembly having a distal end configured to be placed within a brain ventricle for drainage of cerebrospinal fluid, the ingrowth preventing indwelling catheter assembly comprising:

a first segment of porous fiber membrane tubing having a porosity of less than 5 micrometers so as to be impermeable to tissue ingrowth and having a drainage or delivery fluid-flow rate appropriate for an intended application;

a second segment including a non-porous tip having a proximal end attached to a first end of the first segment of porous fiber membrane tubing to form the distal end of the ingrowth preventing indwelling catheter assembly, the proximal end of said second segment terminating at said first end of said first segment;

a third segment of non-porous and flexible tubing having a distal end attached to a second end of the first segment of porous fiber membrane tubing, the distal end of said third segment terminating at said second end of said first segment; and a rigid tubular reinforcement member having a plurality of apertures therethrough disposed within the first segment of porous fiber membrane tubing, said tubular reinforcement member being attached between said second segment including said non-porous tip and said third segment of non-porous and flexible tubing, wherein the distal end of said rigid tubular reinforcement member terminates within the proximal end of said second segment and the proximal end of said rigid tubular reinforcement member terminates within the distal end of said third segment.

* * * * *